(12) United States Patent
Mizuta

(10) Patent No.: US 6,474,350 B1
(45) Date of Patent: Nov. 5, 2002

(54) CLEANING DEVICE FOR PROBE NEEDLE OF PROBE CARD AND WASHING LIQUID USED THEREFOR

(75) Inventor: Masaharu Mizuta, Hyogo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/148,833

(22) Filed: Sep. 4, 1998

(30) Foreign Application Priority Data

Dec. 10, 1997 (JP) ............................................. 9-340105
Apr. 17, 1998 (JP) ........................................... 10-107967

(51) Int. Cl.⁷ ................................................ B08B 3/04
(52) U.S. Cl. ..................... 134/56 R; 134/58 R; 134/88; 134/155; 134/186; 134/184
(58) Field of Search .............................. 134/56 R, 57 R, 134/58 R, 84, 88, 155, 186, 184

(56) References Cited

U.S. PATENT DOCUMENTS

| | | | | |
|---|---|---|---|---|
| 3,710,450 A | * | 1/1973 | Figiel | |
| 4,193,842 A | * | 3/1980 | Rushing | |
| 4,216,671 A | * | 8/1980 | Kurland | |
| 4,314,855 A | * | 2/1982 | Chang et al. | |
| 4,730,631 A | * | 3/1988 | Schwartz | |
| 4,948,563 A | * | 8/1990 | Kanewske, III | |
| 4,971,714 A | * | 11/1990 | Lokkesmoe et al. | |
| 5,011,537 A | * | 4/1991 | Voegele et al. | |
| 5,090,430 A | * | 2/1992 | Nixon | |
| 5,156,813 A | * | 10/1992 | Calhoun | |
| 5,237,385 A | * | 8/1993 | Pfeil et al. | |
| 5,266,121 A | * | 11/1993 | Cioletti | |
| 5,279,794 A | * | 1/1994 | Sasao | |
| 5,339,842 A | * | 8/1994 | Bok | 134/186 |
| 5,489,531 A | * | 2/1996 | Benson | |
| 5,507,923 A | * | 4/1996 | Stouse et al. | |
| 5,896,879 A | * | 4/1999 | Gross et al. | |
| 5,904,899 A | * | 5/1999 | Hayashi | |

FOREIGN PATENT DOCUMENTS

| | | |
|---|---|---|
| JP | 63-298171 | 12/1988 |
| JP | 2-44746 | 2/1990 |
| JP | 3-46247 | 2/1991 |
| JP | 3-50845 | 3/1991 |
| JP | 4-338662 | 11/1992 |
| JP | 8-27297 | 3/1996 |

* cited by examiner

Primary Examiner—Frankie L. Stinson
(74) Attorney, Agent, or Firm—McDermott, Will & Emery

(57) ABSTRACT

A cleaning device for a probe needle of a probe card rarely causing abrasion and deformation of the tip of a probe needle and capable of improving a probe needle life as well as a washing liquid used therefor are obtained. The tip of a probe needle of a probe card is immersed in a washing liquid for a probe needle of a probe card which includes an aqueous solution containing phosphoric acid or an aqueous solution containing chromic acid anhydride and phosphoric acid. While the tip of the probe needle is immersed in the washing liquid, the washing liquid is vibrated by a vibration generating member.

2 Claims, 17 Drawing Sheets

CLEANING DEVICE FOR PROBE NEEDLE OF PROBE CARD AND WASHING LIQUID USED THEREFOR

BACKGROUND OF THE INVENTION

1. Field of the Invention

The present invention relates to a cleaning device for a semiconductor inspection device and a washing liquid used therefor. More specifically, the present invention relates to a cleaning device for a probe needle of a probe card and a washing liquid used therefor.

2. Description of the Background Art

Conventionally, a device called a probe card has been used in the inspection process of semiconductor devices. FIG. 16 is a cross sectional view of a conventional probe card. Referring to FIG. 16, the conventional probe card has an opening 114 formed almost at the center of a substrate 116. In the periphery of opening 114, a plurality of probe needles 111 are provided toward the center of opening 114. Probe needle 111 is connected to a terminal (not shown) arranged in the periphery of substrate 116 through a wiring. In inspecting a semiconductor device, the terminal is connected to an inspection device called a prober. The probe card is arranged opposite to a surface of the semiconductor device to be inspected and is also arranged so that the tip of probe needle 111 comes in contact with an electrode formed on the surface of the semiconductor device. The electrical characteristics of the semiconductor device are thus inspected through probe needle 111 in contact with the electrode formed on the surface of the semiconductor device.

FIG. 17 is a schematic view illustrating conventional probe needle 111 shown in FIG. 16. Referring to FIG. 17, the lead portion of the probe needle has a diameter D of approximately 0.25 mm, the end of the probe needle has a length L of approximately 7 mm, and the tip 112 of the probe needle that comes in contact with an electrode of a semiconductor device has a diameter d of approximately 30 μm. The materials for the probe needle include tungsten or the like.

In inspecting a semiconductor device, tip 112 of the probe needle comes in contact with an electrode 131 formed on a surface of the semiconductor device, as shown in FIGS. 18 and 19. FIGS. 18 and 19 are schematic views illustrating how the tip of the probe needle comes in contact with the electrode formed on the surface of the semiconductor device. As shown in FIG. 18, electrode 131 formed on the surface of semiconductor device 132 is brought in contact with tip 112 of probe needle 111 by raising semiconductor device 132 toward probe needle 111. Electrode 131 of semiconductor device 132 is formed of aluminum, and a thin aluminum oxide layer 133 is formed on a surface of electrode 131. Since aluminum oxide layer 133 is an insulating layer, an aluminum layer 134 under aluminum oxide layer 133 cannot be brought into contact with tip 112 of probe needle 111 simply by pressing tip 112 of probe needle 111 against electrode 131 as shown in FIG. 18. Therefore, current cannot be passed from probe needle 111 to electrode 131.

Accordingly, semiconductor device 132 is typically further raised after tip 112 of probe needle 111 is brought into contact with electrode 131, as shown in FIG. 19. Probe needle 111 is thus elastically deformed and tip 112 of probe needle 111 is horizontally moved on electrode 131. Aluminum oxide layer 133 on the surface of electrode 131 is thus partially removed from the surface of electrode 131 to allow aluminum layer 134 which is the electrode body to come into direct contact with tip 112 of probe needle 111. The process shown in FIG. 19 will be referred to as an overdrive process hereinafter. In this manner, tip 112 of probe needle 111 has come into contact with electrode 131 in the conventional inspection process.

However, the overdrive process as shown in FIG. 19 causes part of aluminum oxide layer 133 removed from the surface of electrode 131 to adhere to tip 112 of probe needle 111 as shown in FIG. 20. When a foreign matter 113, such as aluminum oxide, which is an insulator thus adheres to tip 112 of probe needle 111, foreign matter 113 prevents the electrical connection between tip 112 of probe needle 111 and electrode 131 (see FIG. 19) of the semiconductor device, making it difficult to pass a prescribed current to electrode 131. Accordingly, repeated use of such a probe needle has disadvantageously resulted in an inaccurate inspection of semiconductor devices.

Accordingly, a probe needle cleaning operation has been performed so as to remove foreign matter 113 such as aluminum oxide from tip 112 of probe needle 111.

FIG. 21 is a cross sectional view of an abrasive sheet for probe needles that is used in a conventional probe needle cleaning operation. Referring to FIG. 21, the conventional abrasive sheet 135 for probe needles employs silicon rubber 136 as a matrix, and abrasive grains 137 such as artificial powdery diamond are dispersively arranged in silicon rubber 136. When tip 112 (see FIG. 20) of probe needle 111 (see FIG. 20) is stuck into abrasive sheet 135 prescribed times, foreign matter 113 (see FIG. 20) is scraped off the surface of probe needle 111 by abrasive grains 137 in abrasive sheet 135. Foreign matter 113 has conventionally be removed from tip 112 of probe needle 111 in this manner.

FIG. 22 is a flow chart of a conventional probe needle cleaning operation. Referring to FIG. 22, the conventional probe needle cleaning operation consists of four steps. At step 1, a probe card is arranged opposite to an abrasive sheet. At step 2, the tip of a probe needle is stuck into the abrasive sheet prescribed times. FIG. 23 is a schematic view showing the process of sticking the tip of the probe needle into the abrasive sheet prescribed times at step 2. As shown in FIG. 23, tip 112 of probe needle 111 is stuck into abrasive sheet 135 to allow foreign matter 113 such as aluminum oxide adhered to tip 112 of probe needle 111 to be scraped off by abrasive grains 137 in abrasive sheet 135.

At this stage after step 2, however, a viscous silicon rubber film 138 which is softened silicon rubber 136 (see FIG. 23) as the matrix of abrasive sheet 135 adheres to tip 112 of probe needle 111. A foreign matter 139 also adheres to silicon rubber film 138. Foreign matter 139 includes foreign matter 113 (see FIG. 23) such as aluminum oxide removed from tip 112 of probe needle 111 at step 2, abrasive grains 137 (see FIG. 23) removed from abrasive sheet 135, a removed portion of silicon rubber 136 (see FIG. 23) which is the matrix of abrasive sheet 135, and so on.

Accordingly, the conventional probe needle cleaning operation requires, as step 3, the step of spraying an organic solvent on the tip of the probe needle to remove foreign matter 139 (see FIG. 24) adhering to tip 112. FIG. 25 schematically shows how step 3 is performed.

As shown in FIG. 25, an organic solvent 140 is sprayed on tip 112 of probe needle 111 to dissolve silicon rubber film 138 and to remove silicon rubber film 138 and foreign matter 139 from tip 112 of probe needle 111.

When step 3 is completed, organic solvent 140 remains on probe needle 111 as shown in FIG. 26. Accordingly, the conventional probe needle cleaning operation carries out, as step 4, the step of blowing air to probe needle 111 (see FIG. 26) to dry organic solvent 140 (see FIG. 26) remaining on tip 112 of probe needle 111 and simultaneously blow off foreign matters and the like remaining on the surface of probe needle 111, as shown in FIG. 22.

The conventional probe needle cleaning operation has been performed in this manner.

Conventionally, foreign matter 113 has been removed from tip 112 of probe needle 111 by sticking tip 112 of probe needle 111 into abrasive sheet 135 as shown in FIG. 23. However, when the step of sticking is repeated several hundred times, the side surface and the bottom surface of tip 112 of probe needle 111 have been scraped by abrasive grains 137 in abrasive sheet 135 and tip 112 has been deformed. In the step of sticking, part of probe needle 111 may have been bent, causing variation in the height of tip 112 of probe needle 111.

When tip 112 of probe needle 111 is brought into contact with electrode 131 of semiconductor device 132 as shown in FIGS. 18 and 19, tip 112 of probe needle 111 has been changed in shape and varied in height. In this case, the contact between probe needle 111 and electrode 131 has not been perfect enough, making it difficult to pass a prescribed current to electrode 131.

Such a distorted probe needle needs to be repaired and readjusted by a manufacturer and therefore requires additional maintenance cost. It has been one reason for the increase in the manufacturing cost of a semiconductor device.

SUMMARY OF THE INVENTION

One object of the present invention is to provide a cleaning device for a probe needle of a probe card rarely causing abrasion and deformation of the tip of a probe needle and capable of improving a probe needle life.

Another object of the present invention is to provide a washing liquid used for a cleaning device for a probe needle of a probe card rarely causing abrasion and deformation of the tip of a probe needle and capable of improving a probe needle life.

A washing liquid for a probe needle of a probe card according to a first aspect of the present invention includes an aqueous solution containing phosphoric acid.

Accordingly, when a probe needle is immersed in the washing liquid and vibration is applied to the washing liquid in the cleaning method for a probe needle of a probe card described below, a foreign matter such as aluminum oxide adhering to the probe needle can be removed from the probe needle with little abrasion and deformation of the tip of the probe needle. As a result, abrasion and deformation of the tip of a probe needle in a probe needle cleaning operation can be prevented. Thus, a probe needle life can be improved.

In the washing liquid for a probe needle of a probe card according to the first aspect, the ratio of phosphoric acid with respect to water is preferably 36 milliliters/1 liter.

In the washing liquid for a probe needle of a probe card according to the first aspect, the aqueous solution may further contain chromic acid anhydride.

Accordingly, when the washing liquid is used in the cleaning method for a probe needle of a probe card described below, a foreign matter such as aluminum oxide adhering to a probe needle can be removed more efficiently from the probe needle with little abrasion and deformation of the tip of the probe needle. As a result, abrasion and deformation of the tip of a probe needle in a probe needle cleaning operation can be prevented. Thus, a probe needle life can be improved.

In the washing liquid for a probe needle of a probe card according to the first aspect, the ratio of phosphoric acid with respect to water may be 36 milliliters/1 liter, and the ratio of chromic acid anhydride with respect to water may be 20 grams/1 liter.

A cleaning device for a probe needle of a probe card according to a second aspect of the present invention includes a washing bath for storing a washing liquid for a probe needle including an aqueous solution containing phosphoric acid, and a vibration generating member for vibrating the washing liquid.

Accordingly, when the washing liquid is used, a foreign matter such as aluminum oxide adhering to a probe needle can be removed from the probe needle with little abrasion and deformation of the tip of the probe needle. When the washing liquid is vibrated, the washing liquid can be permeated more reliably into a border portion between a probe needle surface and a foreign matter. As a result, a foreign matter can be removed reliably from the tip of a probe needle, and abrasion and deformation of the tip of a probe needle in a probe needle cleaning operation can be prevented. Thus, a probe needle life can be improved. Further, when the washing liquid is vibrated, a foreign matter can be removed more reliably from the surface of the probe needle by the physical vibration.

In the cleaning device for a probe needle of a probe card according to the second aspect, the ratio of phosphorus acid with respect to water is preferably 36 milliliters/1 liter.

Since the washing liquid suitable for removing a foreign matter such as aluminum oxide from a probe needle is used, a foreign matter can be removed reliably from a probe needle.

A cleaning device for a probe needle of a probe card according to a third aspect of the present invention includes a washing bath for storing a washing liquid for a probe needle including an aqueous solution containing chromic acid anhydride and phosphoric acid.

Accordingly, when the washing liquid is used, a foreign mater such as aluminum oxide adhering to a probe needle can be removed from the probe needle with little abrasion and deformation of the tip of the probe needle. As a result, abrasion and deformation of the tip of a probe needle in a probe needle cleaning operation can be prevented. Thus, a probe needle life can be improved.

The cleaning device for a probe needle of a probe card according to the second or third aspect may further include a post-processing bath for storing a processing liquid for removing the washing liquid from a probe needle.

The cleaning device for a probe needle of a probe card according to the second or third aspect may further include a drying member for drying a probe needle.

In the cleaning device for a probe needle of a probe card according to the third aspect, the ratio of chromic acid anhydride with respect to water is preferably 20 grams/1 liter, and the ratio of phosphoric acid with respect to water is preferably 36 milliliters/1 liter.

Since the washing liquid suitable for removing a foreign matter such as aluminum oxide from a probe needle is used, a foreign matter such as aluminum oxide can be removed more reliably from a probe needle.

The cleaning device for a probe needle of a probe card according to the second or third aspect may further include a vibration generating member for vibrating the washing liquid or the processing liquid.

Since the vibration generating member for vibrating the washing liquid or the processing liquid is thus provided, the washing liquid can be vibrated when part of a probe needle is immersed in the washing liquid. Accordingly, the washing liquid can permeate more reliably into a border portion between a probe needle surface and a foreign matter, further facilitating removal of a foreign matter from the probe needle. At the same time, the physical vibration allows a foreign matter to be removed more reliably from the surface of the probe needle. When the processing liquid is vibrated when part of a probe needle is immersed in the processing liquid, the washing liquid can be removed more reliably from the probe needle.

The cleaning device for a probe needle of a probe card according to the second or third aspect may further include a temperature controlling member for controlling the temperature of the washing liquid.

Accordingly, the temperature of the washing liquid can be controlled so as to keep a temperature suitable for removing a foreign matter from a probe needle. As a result, a foreign matter can be removed from the probe needle more reliably.

The cleaning device for a probe needle of a probe card according to the second or third aspect may further include a distance measuring member for measuring the distance between a probe needle and a washing liquid surface in the washing bath, a position adjusting member for controlling a position of at least either of the probe needle and the washing liquid surface, and a controlling member for controlling the position adjusting member based on information on the measured distance.

Accordingly, the distance between the probe needle and the washing liquid surface can be controlled precisely. As a result, the tip of the probe needle from which a foreign matter needs to be removed can be immersed reliably in the washing liquid. Thus, a foreign matter can be removed more reliably from the probe needle.

In the cleaning device for a probe needle of a probe card according to the second or third aspect, at least one of the washing bath and the post-processing bath may include a member for holding the surface of a portion of the washing liquid or the processing liquid in which a probe needle is immersed higher than the surface other than the portion.

Accordingly, the distance between a portion of the probe card other than the probe needle and the liquid surface can be made larger than the distance between the probe needle and the liquid surface. As a result, the washing liquid or the processing liquid can be prevented from adhering to the portion of the probe card other than the probe needle. It can prevent a probe card failure caused when the washing liquid or the processing liquid adheres to the portion of the probe card other than the probe needle.

A cleaning method for a probe needle of a probe card according to a fourth aspect of the present invention includes the steps of immersing at least part of a probe needle in a washing liquid for a probe needle of a probe card including an aqueous solution containing phosphoric acid, and holding at least part of the probe needle immersed in the washing liquid while vibrating the washing liquid.

Accordingly, a foreign matter such as aluminum oxide adhering to a probe needle can be removed from the probe needle with little abrasion and deformation of the tip of the probe needle. As a result, abrasion and deformation of the tip of a probe needle in a cleaning operation can be prevented. Thus, a probe needle life can be improved.

Since the washing liquid is vibrated, the washing liquid can permeate more reliably into a border portion between a probe needle surface and a foreign matter, further facilitating removal of a foreign matter from the probe needle. At the same time, the physical vibration allows a foreign matter to be removed more reliably from the surface of a probe needle.

In the cleaning method for a probe needle of a probe card according to the fourth aspect, the ratio of phosphoric acid with respect to water is preferably 36 milliliters/1 liter.

Since the washing liquid suitable for removing a foreign matter such as aluminum oxide from a probe needle is used, a foreign matter can be removed reliably from a probe needle.

A cleaning method for a probe needle of a probe card according to a fifth aspect of the present invention includes the steps of heating a washing liquid for a probe needle of a probe card including an aqueous solution containing chromic acid anhydride and phosphoric acid, immersing at least part of a probe needle in the heated washing liquid, and holding at least part of the probe needle immersed in the washing liquid.

Accordingly, a foreign matter such as aluminum oxide adhering to a probe needle can be removed from the probe needle with little abrasion and deformation of the tip of probe needle. As a result, abrasion and deformation of the tip of a probe needle in a cleaning operation can be prevented. Thus, a probe needle life can be improved.

In the cleaning method for a probe needle of a probe card according to the fifth aspect, the temperature for heating the washing liquid is at least 95° C. and the time for holding at least part of the probe needle immersed in the washing liquid is at least 10 minutes.

Accordingly, a foreign matter such as aluminum oxide can be removed more reliably from a probe needle.

In the cleaning method for a probe needle of a probe card according to the fifth aspect, the ratio of chromic acid anhydride with respect to water is preferably 20 grams/1 liter, and the ratio of phosphoric acid with respect to water is preferably 36 milliliters/1 liter.

The cleaning method for a probe needle of a probe card according to the fourth or fifth aspect may further include the steps of measuring the distance between a probe needle and a washing liquid surface, and controlling a position of at least either of the probe needle and the washing liquid surface based on information on the measured distance.

Accordingly, the distance between the probe needle and the washing liquid surface can be controlled more precisely. As a result, the portion of the probe needle to be cleaned can be immersed reliably in the washing liquid. Thus, a foreign matter such as aluminum oxide can be removed more reliably from a probe needle.

The cleaning method for a probe needle of a probe card according to the fifth aspect may further include the step of vibrating the washing liquid when at least part of the probe needle is immersed in the washing liquid.

When the washing liquid is thus vibrated, the washing liquid can permeate further in a border portion between a probe needle surface and a foreign matter, further facilitating removal of a foreign matter. At the same time, the physical vibration of the washing liquid allows more reliable removal of a foreign matter from the surface of a probe needle.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

The embodiments of the present invention will be described below with reference to the drawings.

First Embodiment

Figure 1:
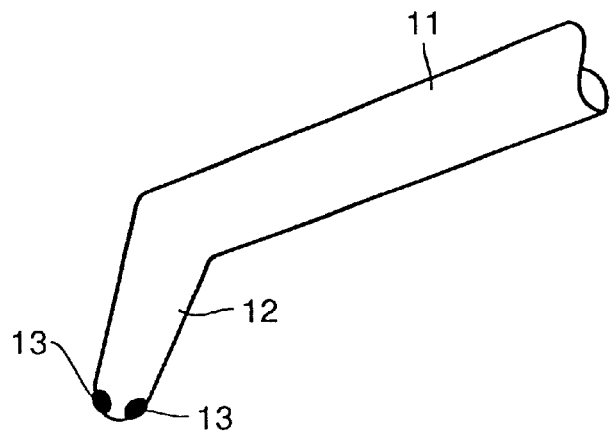
FIG. 1 schematically shows a foreign matter adhering to the tip of a probe needle.
Figure 2:
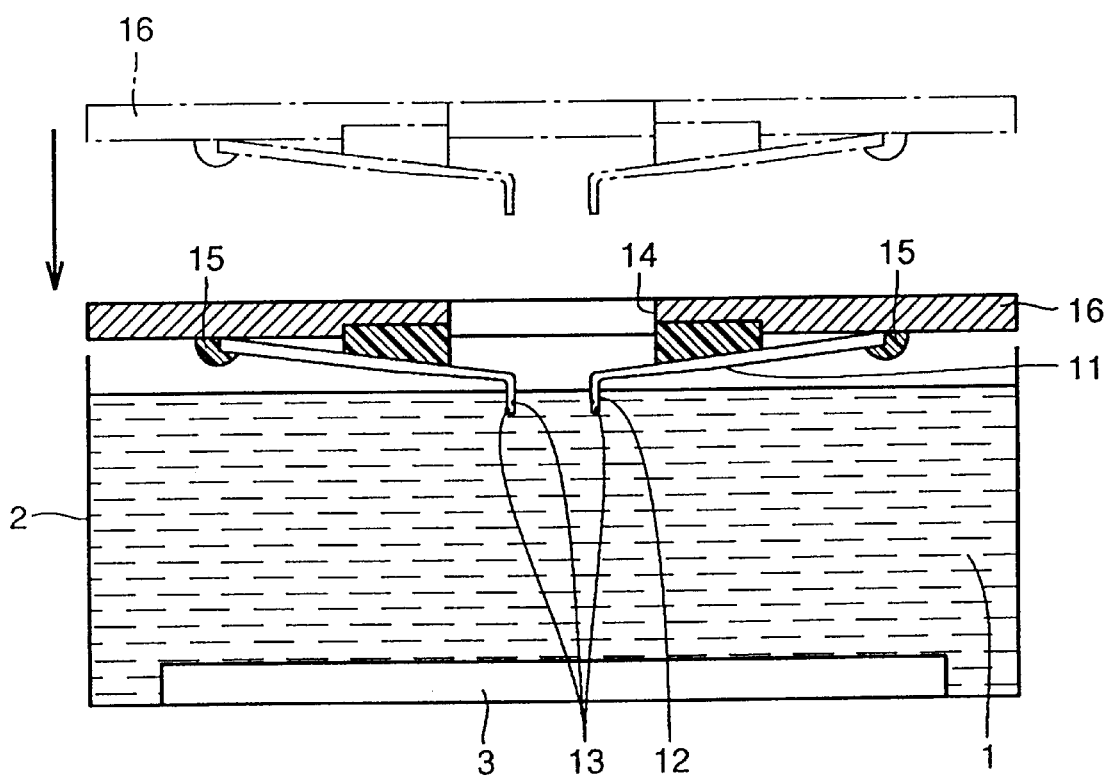
FIGS. 2 to 4 schematically show first to third steps of a cleaning operation for a probe needle of a probe card according to a first embodiment of the present invention.

Referring to FIG. 1, a foreign matter 13 such as aluminum oxide has adhered to the tip 12 of a probe needle 11. Referring to FIG. 2, at a first step of a cleaning operation for a probe needle of a probe card according to a first embodiment of the present invention, a washing liquid 1 is maintained in a washing bath 2. Washing liquid 1 is an aqueous solution containing chromic acid anhydride and phosphoric acid. In the washing liquid, the ratio of chromic acid anhydride with respect to water is 20 grams/1 liter, and the ratio of phosphoric acid with respect to water is 36 milliliters/1 liter. The bottom surface of washing bath 2 is provided with an electric heater 3 for heating washing liquid 1.

A probe card is then prepared over washing bath 2 to oppose to it. The probe card has an opening 14 formed almost at the center of a substrate 16. In the periphery of opening 14, a plurality of probe needles 11 are provided toward the center of opening 14. Probe needle 11 is connected to a terminal (not shown) arranged in the periphery of substrate 16 through a wiring. Probe needle 11 is fixed to substrate 16 with resin 15. As shown in FIG. 1, foreign matter 13 has adhered to tip 2 of probe needle 11.

As shown in FIG. 2, tip 12 of probe needle 11 with foreign matter 13 adhered is then immersed in washing liquid 1. The temperature of washing liquid 1 at this time is kept at least 95° C. (boiling state). Although the effect of removing a foreign matter can be obtained even when the temperature of washing liquid 1 is 95° C. or less, a more remarkable effect can be achieved when the temperature of washing liquid 1 is at least 95° C. Tip 12 of probe needle 11 is immersed in washing liquid 1 for 10 minutes. Thus, foreign matter 13 is removed from tip 12 of probe needle 11. After the first step of the cleaning operation shown in FIG. 2, washing liquid 1 remains on tip 12 of probe needle 11. Accordingly, washing liquid 1 remaining on tip 12 of probe needle 11 is rinsed away such as by alcohol, as shown in FIG. 3.

Figure 3:
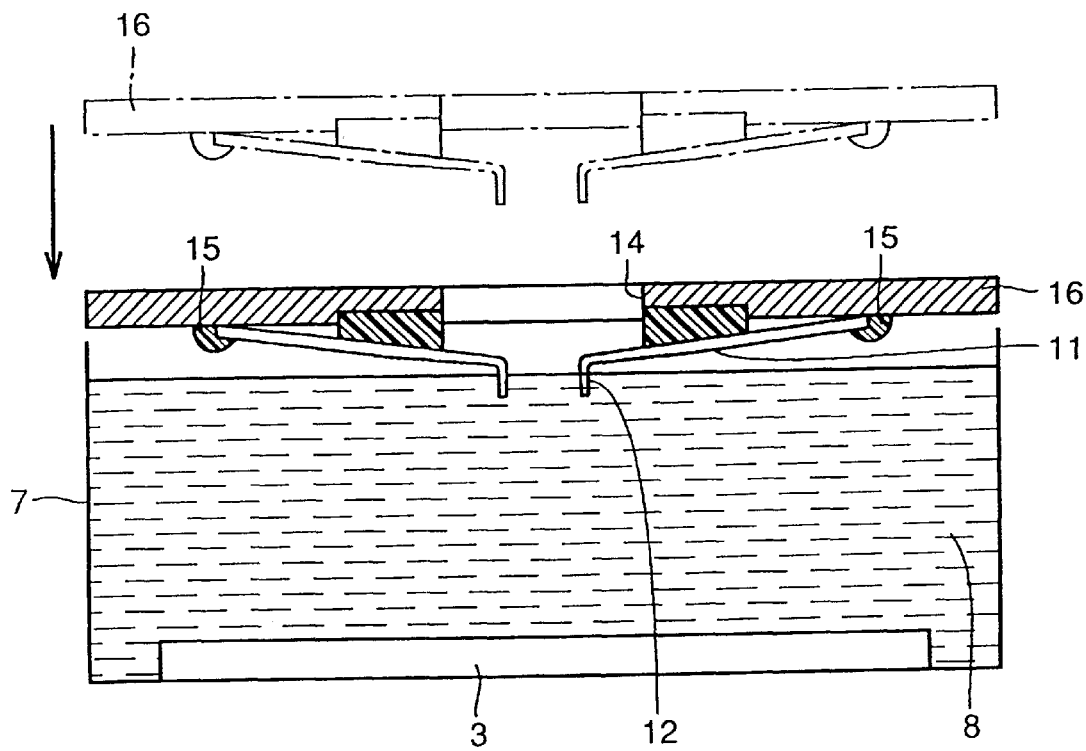

Referring to FIG. 3, a post-processing bath 7 is filled with a processing liquid 8 such as alcohol. Electric hater 3 for heating processing liquid 8 is provided on the bottom surface of post-processing bath 7. Here, electric heater 3 may not necessarily be provided. Similarly to the step shown in FIG. 2, tip 12 of probe needle 11 is immersed in processing liquid 8 to remove washing liquid 1 (see FIG. 2) remaining on tip 12 of probe needle 11.

Figure 4:
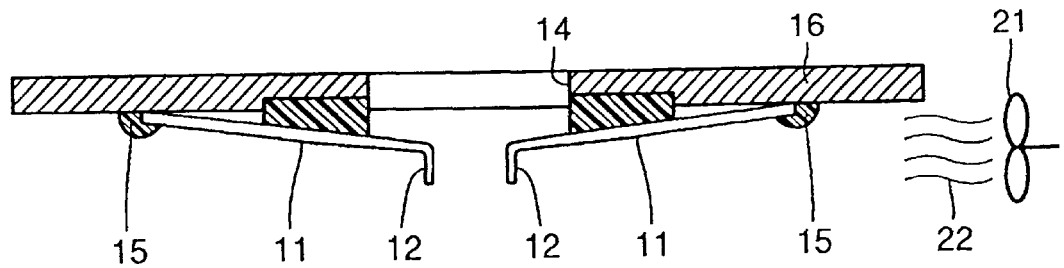

After the step shown in FIG. 3, air 22 is blown to tip 12 of probe needle 11 using a blower 21 as shown in FIG. 4 to dry processing liquid 8 (see FIG. 3) such as alcohol remaining on tip 12 of probe needle 11.

The cleaning operation for a probe needle of a probe card according to the first embodiment of the present invention is performed in this manner.

Here, a test was conducted by changing the time for immersing tip 12 (see FIG. 2) of probe needle 11 (see FIG. 2) in washing liquid 1 (see FIG. 2) at the first step (shown in FIG. 2) of the cleaning operation for a probe needle of a probe card according to the first embodiment of the present invention. The result is shown in Table 1.

TABLE 1

| Sample No. | Time (minutes) for immersing in washing liquid (aqueous solution of chromic acid anhydride and phosphoric acid) | State of foreign matter removal after cleaning operation |
| --- | --- | --- |
| 1 | 5 | X |
| 2 | 10 | ○ |
| 3 | 20 | ○ |

As testing conditions, washing liquid 1 which was used was an aqueous liquid containing chromic acid anhydride and phosphoric acid as described above, the ratio of chromic acid anhydride with respect to water was 20 grams/1 liter, and the ratio of phosphoric acid with respect to water was 36 milliliters/1 liter. Further, the temperature of washing liquid 1 was at least 95° C. (boiling state). The time for immersing tip 12 of probe needle 11 in washing liquid 1 was 5 minutes, 10 minutes or 20 minutes. After the cleaning operation was carried out, the state of remaining foreign matter 13 (see FIG. 2) on tip 12 of probe needle 11 was observed by an SEM (Scanning Electron Microscope) and an EPMA (Electron Probe Microanalysis).

As can also be seen from Table 1, in the case of the sample when the immersing time was 5 minutes, a foreign matter such as aluminum oxide remained on tip 12 of probe needle 11 even after the cleaning operation. With respect to the samples when the immersing time was 10 or 20 minutes, foreign matter 13 was removed from tip 12 of probe needle 11 after the cleaning operation. Since the step of sticking probe needle 11, for example, in an abrasive sheet was not performed, abrasion and deformation of tip 12 of probe needle 11 was not caused.

By thus using washing liquid 1, foreign matter 13 such as aluminum oxide adhering to the surface of tip 12 of probe needle 11 can be removed while preventing abrasion and deformation of tip 12 of probe needle 11. Thus, a probe need life can be improved.

Figure 5:
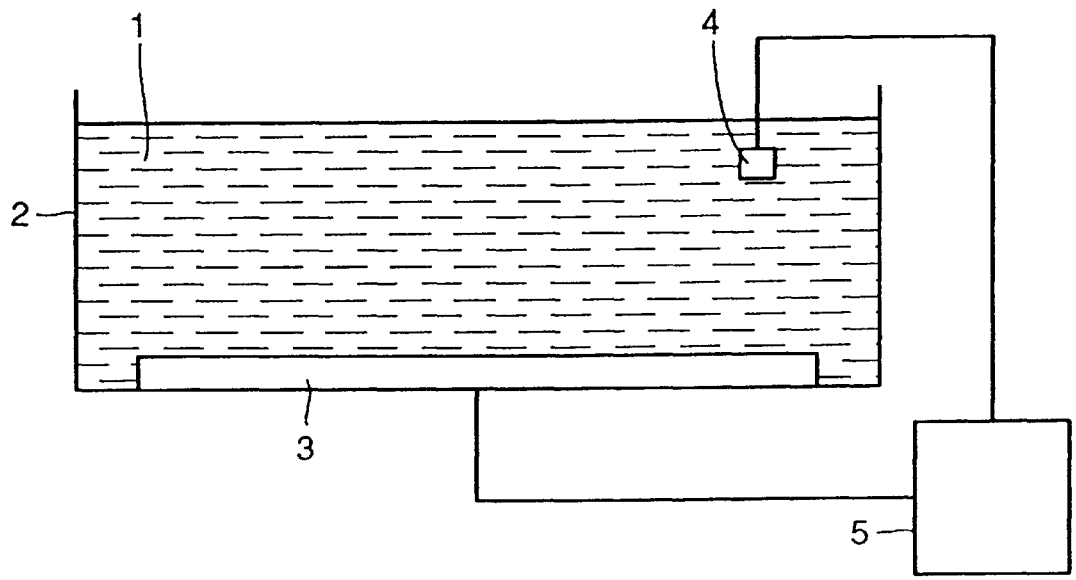
FIG. 5 schematically shows a first variation of the washing bath used at the first step of the FIG. 2 cleaning operation for a probe needle of a probe card according to the first embodiment of the present invention.

As shown in FIG. 5, in the cleaning operation for a probe needle of a probe card according to the first embodiment of the present invention, washing bath 2 may include a temperature sensor 4 for measuring the temperature of washing liquid 1, and a controller 5 having controlling means for controlling ON/OFF of electric heater 3 based on the temperature of washing liquid 1 measured by temperature sensor 4.

Accordingly, the temperature of washing liquid 1 can be managed precisely, and the temperature of washing liquid 1 can be kept in a range optimum for the cleaning operation when foreign matter 13 is to be removed from tip 12 of probe needle 11. As a result, removal of foreign matter 13 from probe needle 11 can be further facilitated.

Figure 6:
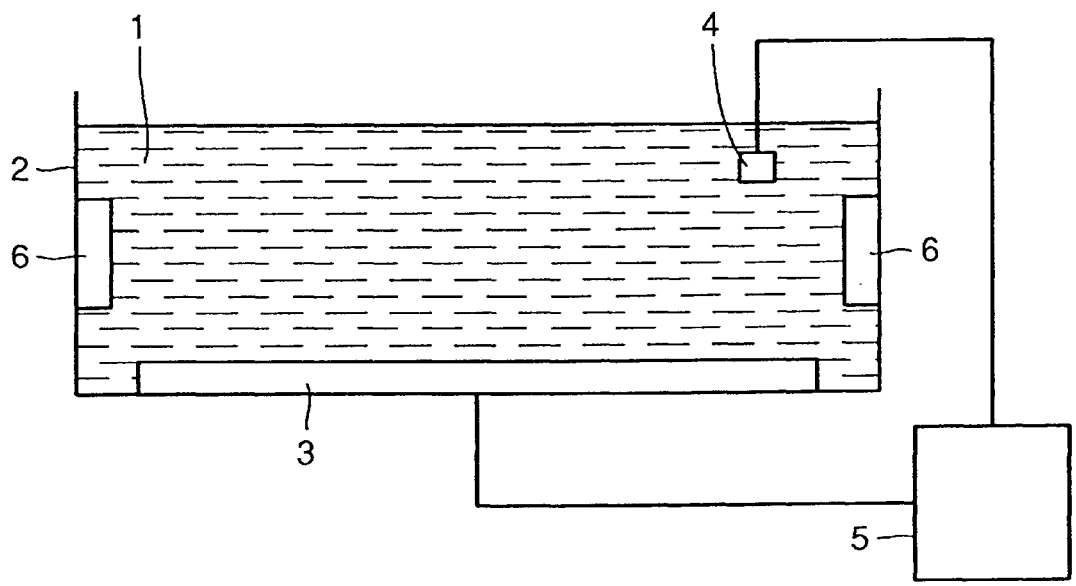
FIG. 6 schematically shows a second variation of the washing bath used at the first step of the FIG. 2 cleaning operation for a probe needle of a probe card according to the first embodiment of the present invention.

In the cleaning operation for a probe needle of a probe card according to the first embodiment of the present invention, washing bath 2 may include an ultrasonic generating device 6 as shown in FIG. 6.

Referring to FIG. 6, ultrasonic generating device 6 is provided on a side surface of washing bath 2 used in the cleaning operation for a probe needle of a probe card according to the first embodiment of the present invention. Accordingly, when tip 12 of probe needle 11 is immersed in washing liquid 1 to remove foreign matter 13, the washing liquid can be permeated further into a border portion between the surface of probe needle 11 and foreign matter 13 by vibrating washing liquid 1 using ultrasonic generating device 6. Thus, removal of foreign matter 13 can be further facilitated. At the same time, the physical vibration caused by the ultrasonic waves allows foreign matter 13 to be removed more reliably from the surface of tip 12 of probe needle 11.

Second Embodiment

Figure 7:
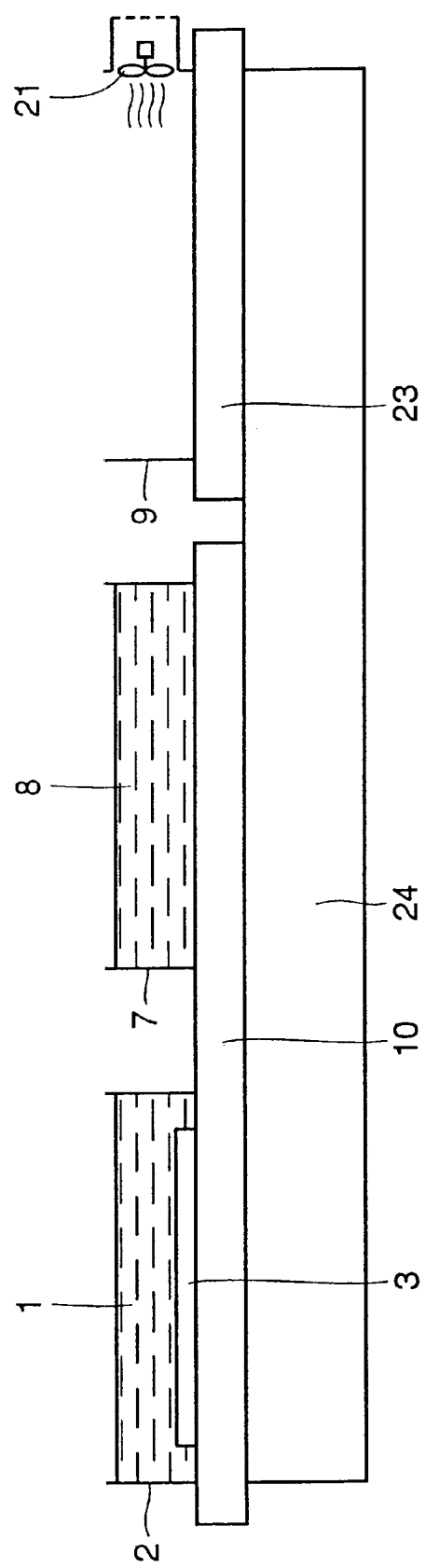
FIG. 7 schematically shows a cleaning device for a probe needle of a probe card according to a second embodiment of the present invention.

Referring to FIG. 7, a cleaning device for a probe needle of a probe card according to a second embodiment of the present invention includes a stand 24 for the entire cleaning device, an ultrasonic generating device 10, a fixing stand 23, a washing bath 2, a post-processing bath 7 and a drying chamber 9. An electric heater 3 is provided on the bottom surface of washing bath 2. Washing bath 2 may include a temperature sensor 4 and a temperature controlling device 5 as shown in FIG. 5. Washing bath 2 is filled with a washing liquid 1 having the same composition as the washing liquid used in the first embodiment. Post-processing bath 7 is filled with a processing liquid 8 such as alcohol. A side surface of drying chamber 9 is provided with a blower 21 for drying the surface of a probe needle. A probe needle with a foreign matter adhered can successively be immersed in washing liquid 1 in washing bath 2 and processing liquid 8 such as alcohol in post-processing bath 7.

Accordingly, a foreign matter can be removed from a probe needle with little abrasion and deformation of the tip of the probe needle. As a result, deformation and abrasion of the tip of a probe needle can be prevented, and a probe needle life can be improved.

Then, the surface of a probe needle can be dried by blowing air to the probe needle in drying chamber 9 using blower 21. By applying vibration to washing liquid 1 and processing liquid 8 using vibration generating device 10 when a probe needle is immersed in washing liquid 1 and processing liquid 8, removal of a foreign matter from a probe needle can be further facilitated. Furthermore, washing liquid 1 can be heated by electric heater 3.

Figure 8:
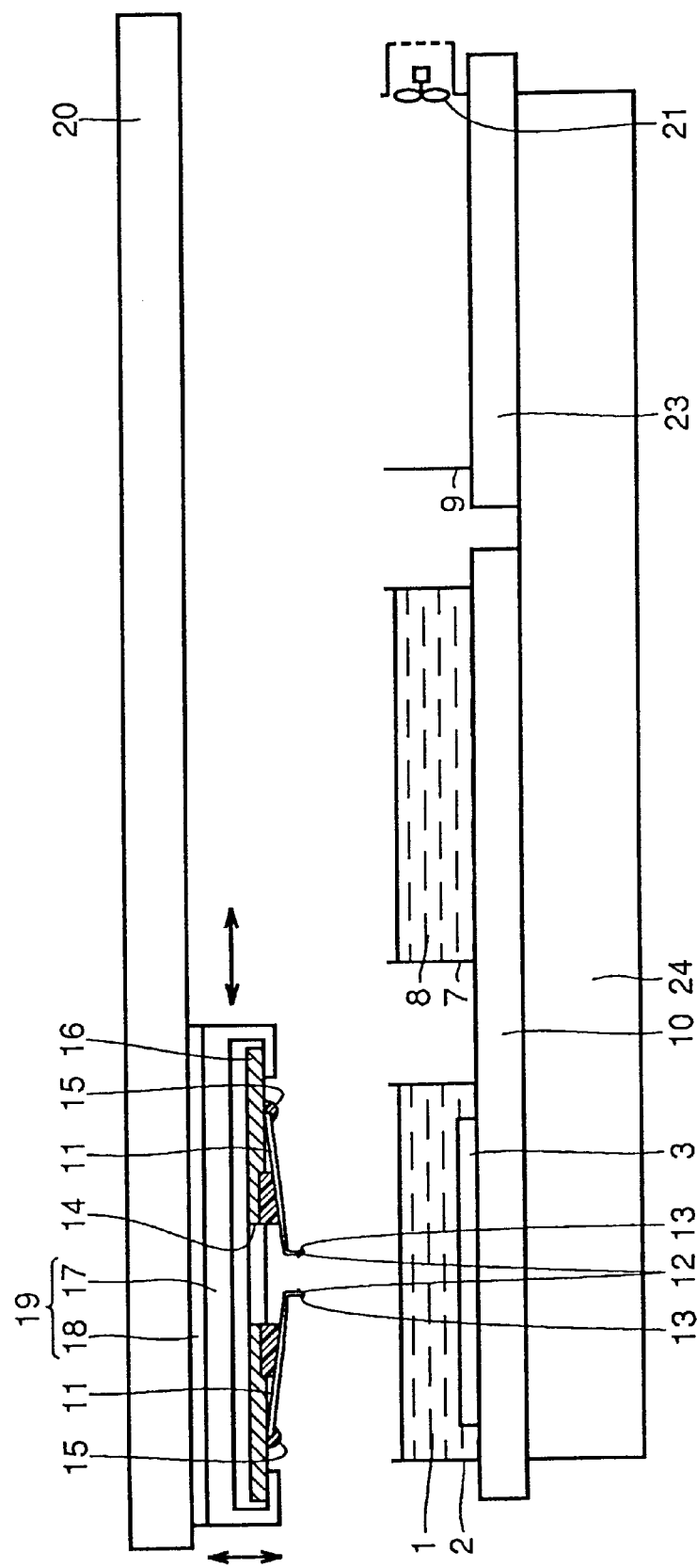
FIG. 8 schematically shows a first variation of the FIG. 7 cleaning device for a probe needle of a probe card according to the second embodiment of the present invention.

Referring to FIG. 8, a first variation of the cleaning device for a probe needle of a probe card according to the second embodiment of the present invention basically includes the same structure as the cleaning device for a probe needle of a probe card shown in FIG. 7. In the first variation, however, a probe card holding member 19 and a holding member guiding portion 20 are provided over washing bath 2, post-processing bath 7 and drying chamber 9. Probe card holding member 19 includes a base portion 18 and a up/down moving portion capable of moving upward and downward. Probe card holding member 19 can move horizontally along holding member guiding portion 20. Up/down moving portion 17 of probe card holding member 19 holds a probe card having probe needle 11 to be cleaned.

The probe card has an opening 14 formed almost at the center of a substrate 16. In the periphery of opening 14, a plurality of probe needles 11 are provided toward the center of opening 14. Probe needle 11 is connected to a terminal (not shown) arranged in the periphery of substrate 16 through a wiring. Probe needle 11 is fixed to substrate 16 with fixing resin 15. A foreign matter 13 has adhered to the surface of tip 12 of probe needle 11.

Figure 9:
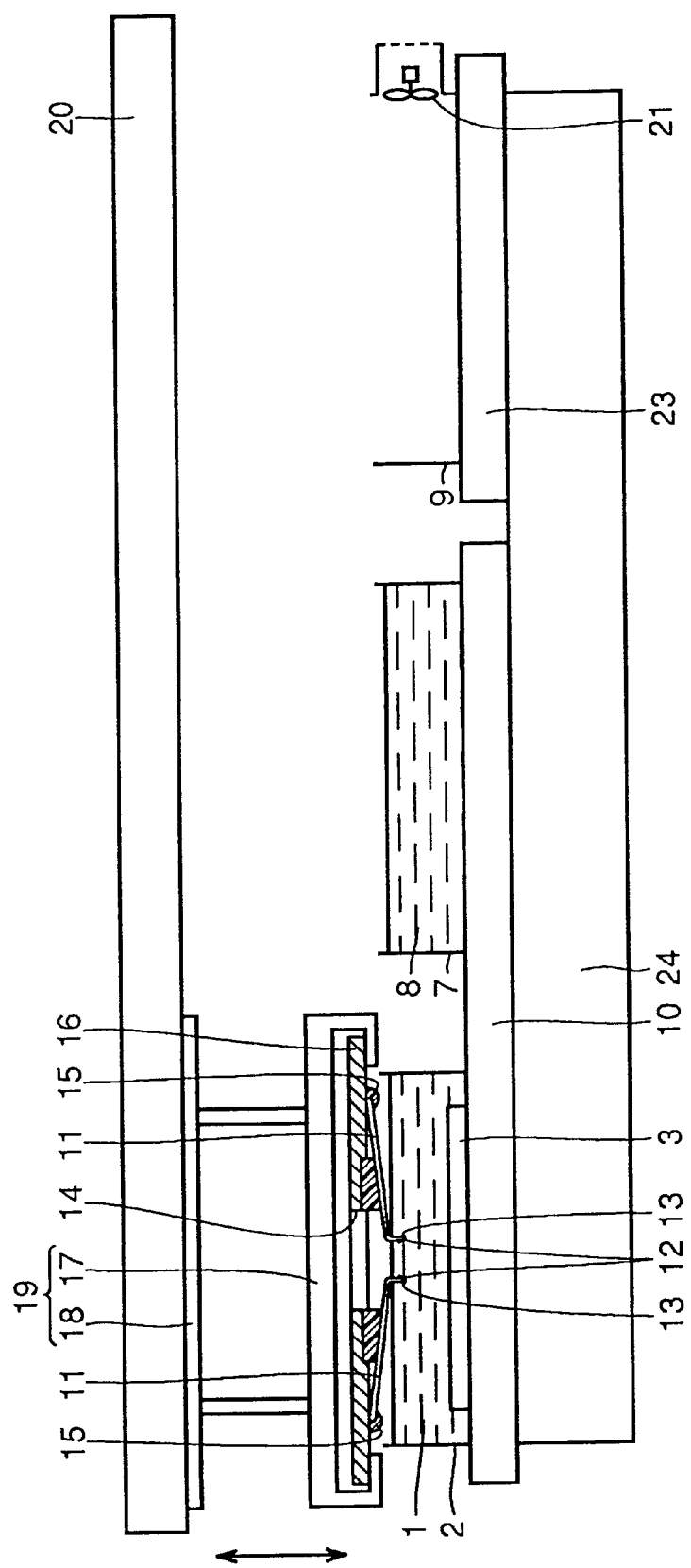
FIGS. 9 to 11 schematically show first to third steps of a cleaning operation for a probe needle using the FIG. 8 first variation of the cleaning device for a probe needle of a probe card according to the second embodiment of the present invention.
Figure 10:
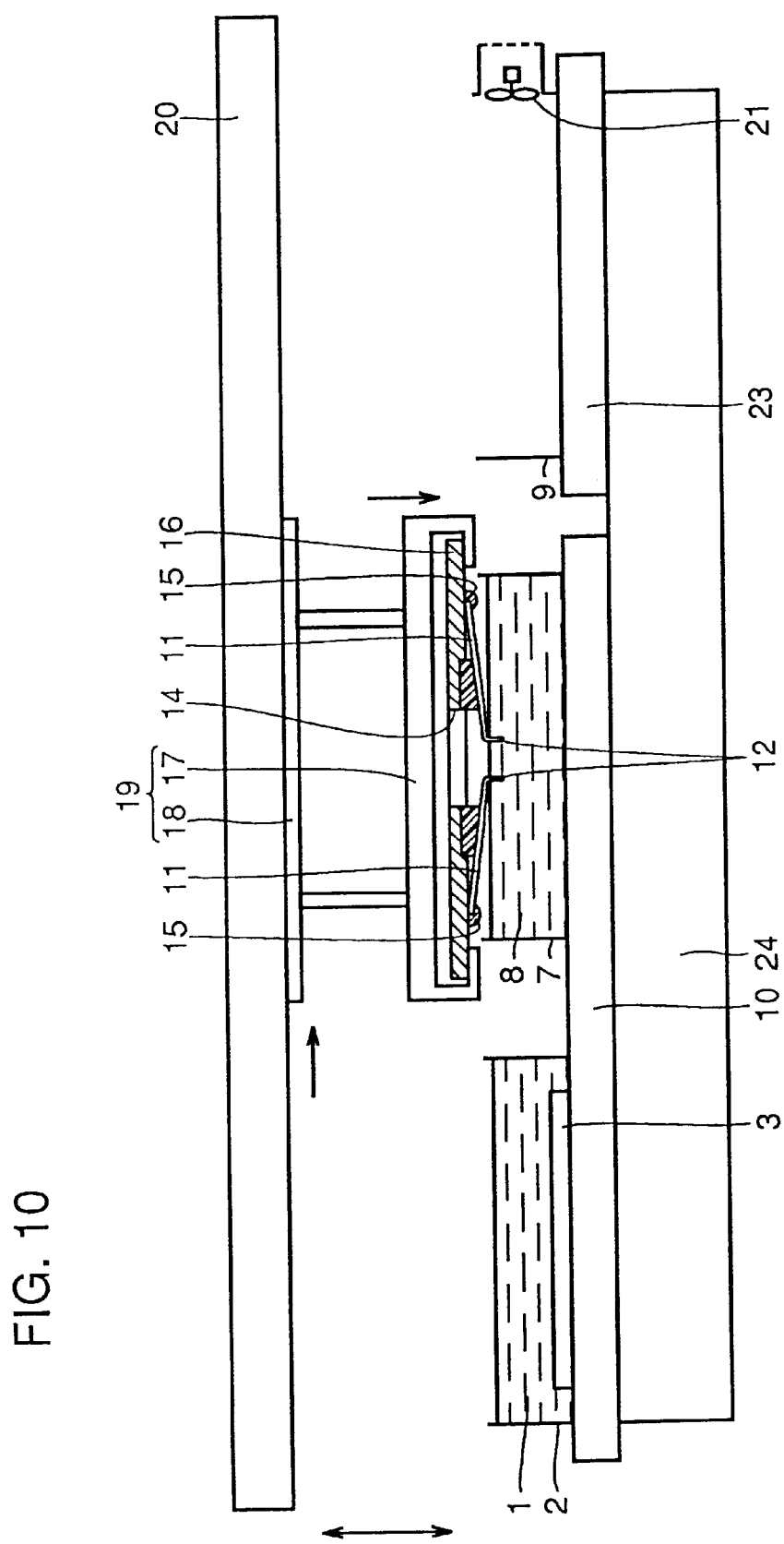
Figure 11:
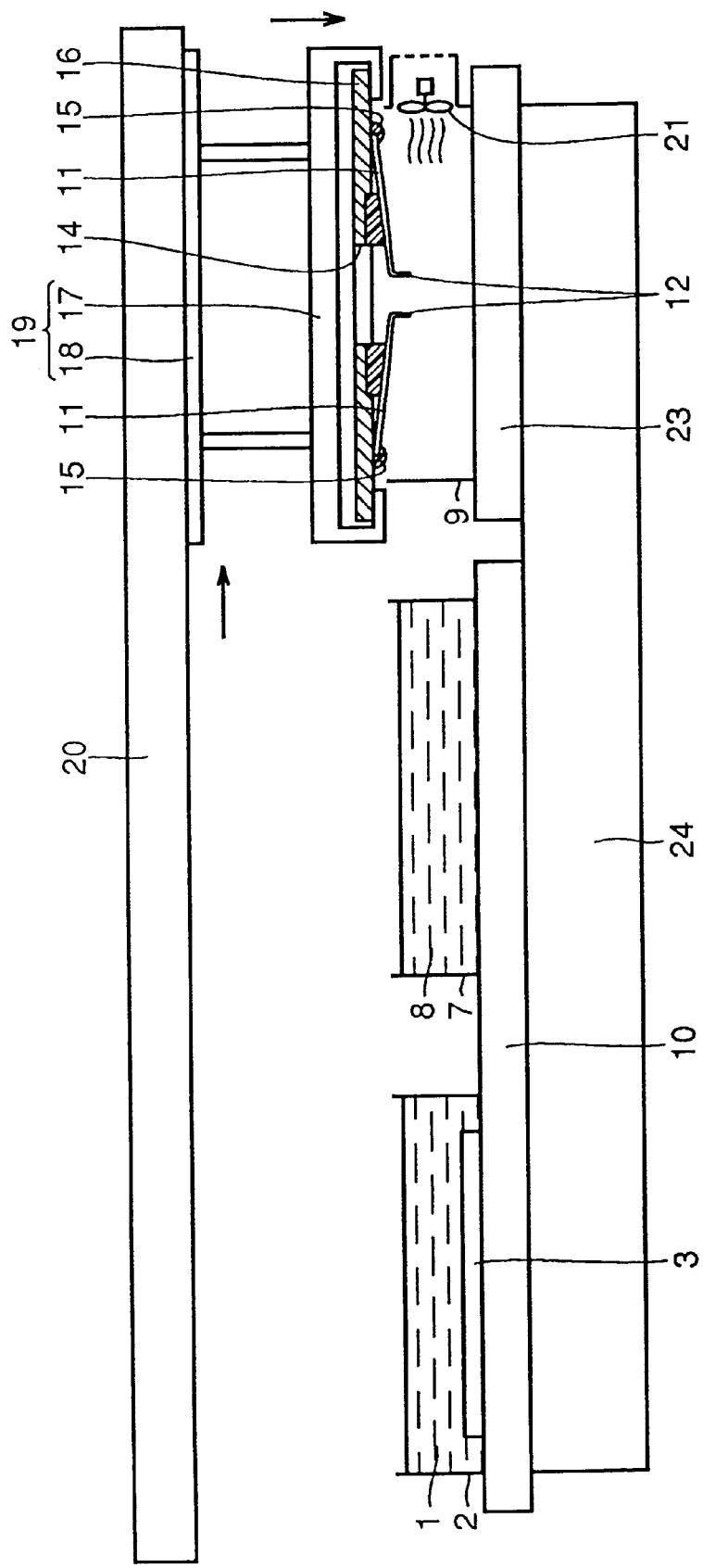

Referring to FIGS. 9 to 11, a cleaning operation for a probe needle using the variation of the cleaning device according to the second embodiment of the present invention will be described below.

As shown in FIG. 9, probe card holding member 19 is firstly moved along holding member guiding portion 20 so as to be positioned over washing bath 2. Up/down moving portion 17 holding a probe card is then moved downward to immerse tip 12 of probe needle 11 in washing liquid 1. This state is maintained for approximately 10 minutes. In this case, washing liquid 1 is kept at least 95° C. (boiling state), and vibration is applied to washing liquid 1 by vibration generating device 10. Since foreign matter 13 is thus removed from tip 12 of probe needle 11 using washing liquid 1, deformation and abrasion of tip 12 of probe needle 11 can be prevented unlike the case using a conventional abrasive sheet.

After the washing operation is completed and up/down moving portion 17 moves upward, probe card holding member 19 moves horizontally along holding member guiding portion 20 to reach a region over post-processing bath 7. As shown in FIG. 10, up/down moving portion 17 moves downward to immerse tip 12 of probe needle 11 with washing liquid 1 remained in processing liquid 8 such as alcohol. In this case, vibration may be applied to processing liquid 8 by vibration generating device 10. Washing liquid 1 is rinsed from tip 12 of probe needle 11 in this manner.

After up/down moving portion 17 moves upward, probe card holding member 19 moves horizontally along holding member guiding portion 20 to reach a region over drying chamber 9. As shown in FIG. 11, up/down moving portion 17 moves downward to place tip 12 of probe needle 11 in drying chamber 9. In drying chamber 9, processing liquid 8 such as alcohol remaining on tip 12 of probe needle 11 is removed by air blown to tip 12 of probe needle 11 using blower 21.

Figure 12:
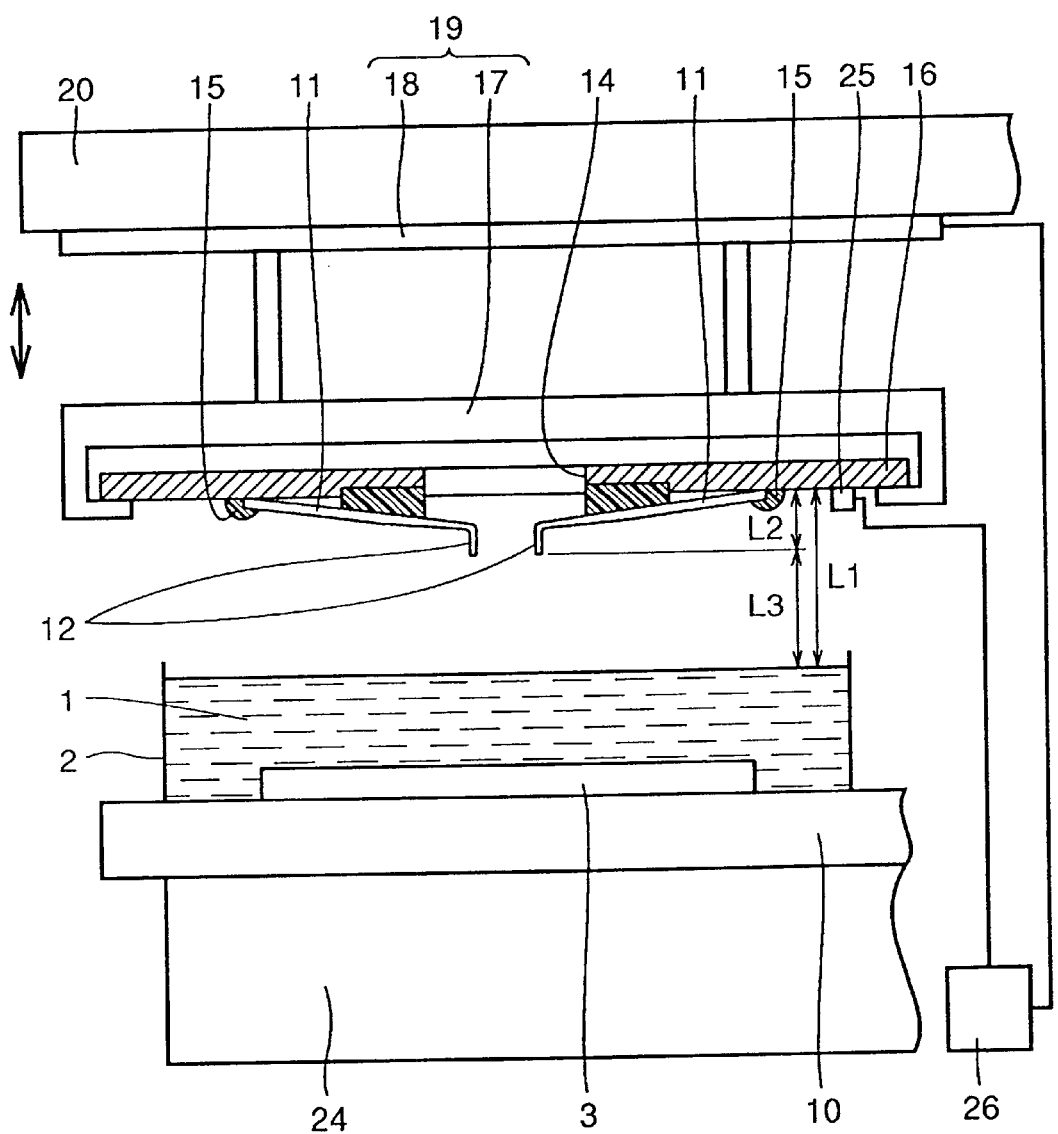
FIG. 12 is a partially enlarged view showing a second variation of the FIG. 7 cleaning device for a probe needle of a probe card according to the second embodiment of the present invention.

Referring to FIG. 12, a second variation of the cleaning device for a probe needle of a probe card according to the second embodiment of the present invention basically includes the same structure as the first variation shown in FIG. 8. However, the second variation includes a distance sensor 25 provided on a surface of probe card substrate 16, and a controlling member 26 having controlling means for controlling the operation of up/down moving portion 17 of probe card holding member 19 based on data output from distance sensor 25.

Since distance sensor 25 is thus provided, the distance L1 between probe card substrate 16 and the surface of processing liquid 1 can be measured in the second variation of the cleaning device for a probe needle of a probe card according to the second embodiment of the present invention. Since the distance L2 from the surface of probe card substrate 16 to tip 12 of probe needle 11 is known, the distance L3 between tip 12 of probe needle 11 and the surface of washing liquid 1 can be found. By controlling the operation of up/down moving portion 17 based on the information, tip 12 of probe needle 11 can reliably be immersed in washing liquid 1.

Accordingly, a foreign matter can be removed more reliably from tip 12 of probe needle 11. Since excessive downward motion of up/down moving portion 17 can be prevented, washing liquid 1 can also be prevented from adhering, for example, to substrate 16 and resin 15 for fixing probe needle 11 in a probe card.

Figure 13:
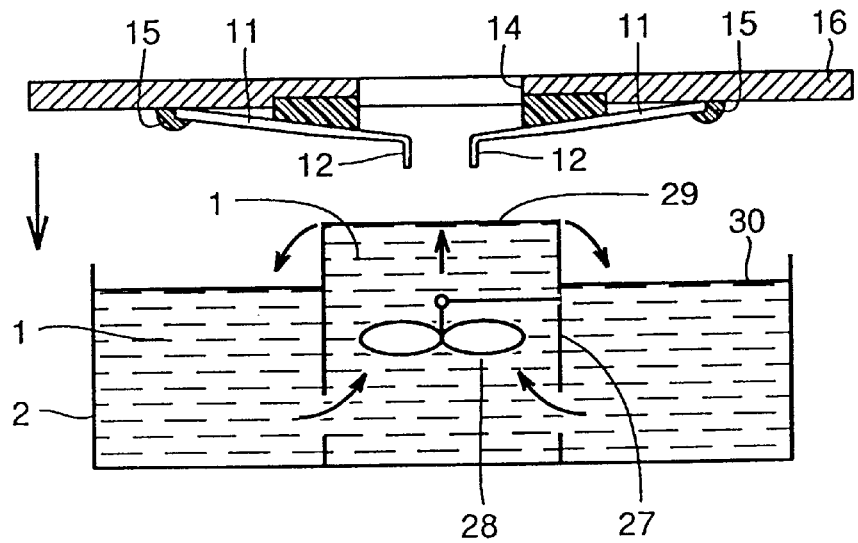
FIG. 13 schematically shows a variation of the washing bath of the FIG. 7 cleaning device for a probe needle of a probe card according to the second embodiment of the present invention.

Referring to FIG. 13, a variation of washing bath 2 in the cleaning device for a probe needle of a probe card according to the second embodiment of the present invention includes inner walls 27 and a liquid supplying member 28 for supplying washing liquid 1 into the interior surrounded by inner walls 27. Liquid supplying member 28 may include a propeller type member as shown in FIG. 13 and use another pump for liquid.

By thus constructing the variation of washing bath 2 shown in FIG. 13, washing liquid 1 which is received from the lower portion of inner walls 27 to a region surrounded by inner walls 27 by liquid supplying member 28 is overflowed from the upper portion of inner walls 27. Accordingly, the surface 29 of washing liquid 1 in the region surrounded by inner walls 27 can be held higher than the surface 30 of washing liquid 1 other than the region surrounded by inner walls 27. Therefore, by arranging a probe card so as to immerse tip 12 of probe needle 11 in the region surrounded by inner walls 27, the distance between probe card substrate 16 and surface 30 of processing liquid 1 which is not in the vicinity of tip 12 of probe needle 11 can be made larger than the distance between substrate 16 and surface 29 of washing liquid 1 in the vicinity of tip 12 of probe needle 11. As a result, washing liquid 1 can be prevented from adhering to probe card substrate 16, resin 15 for fixing a probe needle, and the like. Accordingly, a damage to a probe card by adhered washing liquid 1 can be prevented.

Washing liquid 1 always flows in the interior of inner walls 27. Accordingly, fresh washing liquid 1 always comes in contact with tip 12 of probe needle 11 which is immersed. As a result, a foreign matter can be removed more efficiently from tip 12 of probe needle 11.

Third Embodiment

Figure 14:
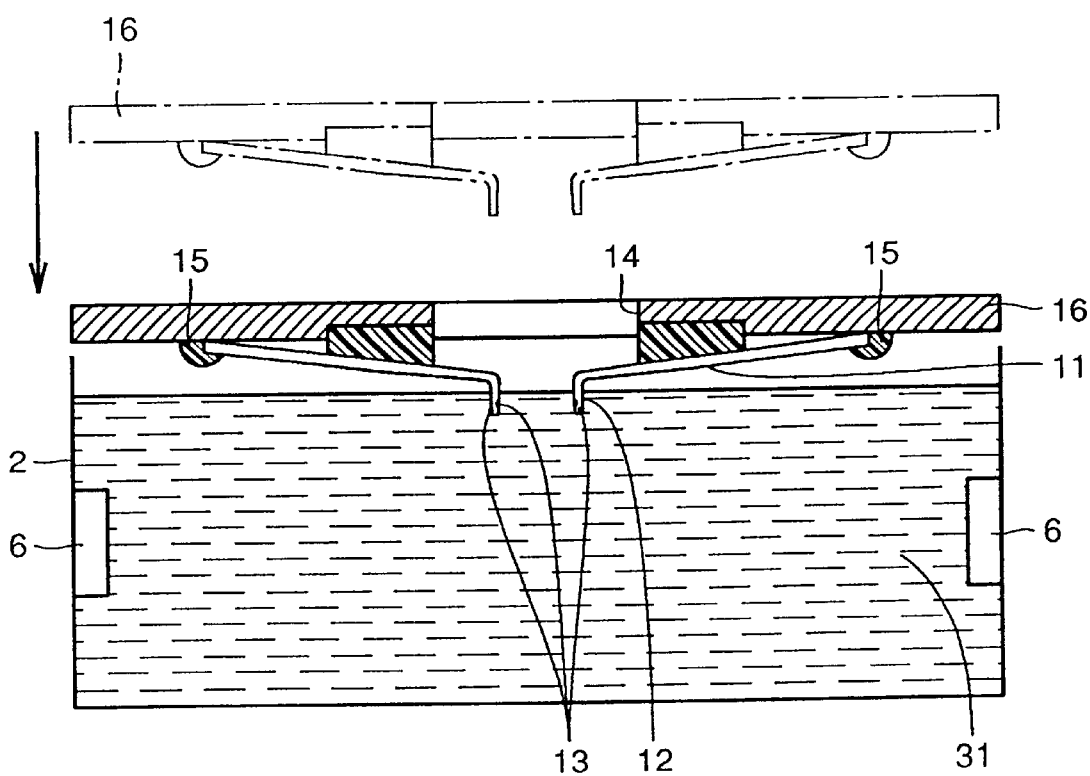
FIG. 14 schematically shows a cleaning operation for a probe needle of a probe card according to a third embodiment of the present invention.

Referring to FIG. 14, a washing liquid 31 is maintained in a washing bath 2 at a first step of a cleaning operation for a probe needle of a probe card according to a third embodiment of the present invention. Washing liquid 31 is an aqueous solution containing phosphoric acid. The ratio of phosphoric acid with respect to water is 36 milliliters/1 liter. An ultrasonic generating device 6 for applying vibration to washing liquid 31 is provided on a side surface of washing bath 2. A probe card is prepared over washing bath 2 to oppose to it. The probe card has the same structure as the probe card shown in FIG. 2. A foreign matter 13 has adhered to the tip 12 of a probe needle 11 of the probe card.

As shown in FIG. 14, tip 12 of probe needle 11 with foreign matter 13 adhered is immersed in washing liquid 31. The temperature of washing liquid 31 at this time is of a normal temperature. Tip 12 of probe needle 11 is immersed in washing liquid 31 for 10 minutes. Ultrasonic generating device 6 applies vibration to washing liquid 31 while tip 12 of probe needle 11 is immersed in washing liquid 31. Accordingly, washing liquid 31 can be permeated further into a border portion between the surface of probe needle 11 and foreign matter 13.

By thus using washing liquid 31, foreign matter 13 such as aluminum oxide adhering to the surface of tip 12 of probe needle 11 can be removed while preventing abrasion and deformation of tip 12 of probe needle 11. Further, by applying vibration using ultrasonic generating device 6, removal of foreign matter 13 can be facilitated and, at the same time, a foreign matter can be removed from the surface of tip 12 of probe needle 11 more reliably by the physical vibration of the ultrasonic waves.

Similarly to the washing bath 2 shown in FIG. 2, washing bath 2, shown in FIG. 14, according to the third embodiment of the present invention may include an electric heater.

After the step shown in FIG. 14, the second and third steps, shown in FIGS. 3 and 4, of the cleaning operation for a probe needle of a probe card according to the first embodiment are performed.

The cleaning operation for a probe needle of a probe card according to the third embodiment of the present invention is performed in this manner.

Here, a test was conducted by changing the time for immersing tip 12 of probe needle 11 in washing liquid 31 at the first step, shown in FIG. 14, of the cleaning operation for a probe needle of a probe card according to the third embodiment of the present invention. The result is shown in Table 2.

TABLE 2

| Sample No. | Time (minutes) for immersing in washing liquid (aqueous solution of phosphoric acid) | State of foreign matter removal after cleaning operation |
|---|---|---|
| 1 | 5 | X |
| 2 | 10 | ○ |
| 3 | 20 | ○ |

As testing conditions, washing liquid 31 which was used was an aqueous solution containing phosphoric acid as described above, the ratio of phosphoric acid with respect to water was 36 milliliters/1 liter, and washing liquid 31 was at a normal temperature. The time for immersing tip 12 of probe needle 11 in washing liquid 31 was 5 minutes, 10 minutes or 20 minutes. After the cleaning operation is performed, the state of remaining foreign matter 13 (see FIG. 14) on tip 12 of probe needle 11 was observed by an SEM and an EPMA similarly to the test in the first embodiment of the present invention.

As can also be seen from Table 2, in the case of the sample when the washing time was 5 minutes, a foreign matter such as aluminum oxide remained on tip 12 of probe needle 11 even after the cleaning operation. With respect to the samples when the immersing time was 10 minutes or 20 minutes, however, foreign matter 13 was removed from tip 12 of probe needle 11 after the cleaning operation.

Since the step of sticking probe needle 11, for example, in an abrasive sheet was not performed unlike in a conventional case, abrasion and deformation of tip 12 of probe needle 11 was not caused.

Fourth Embodiment

Figure 15:
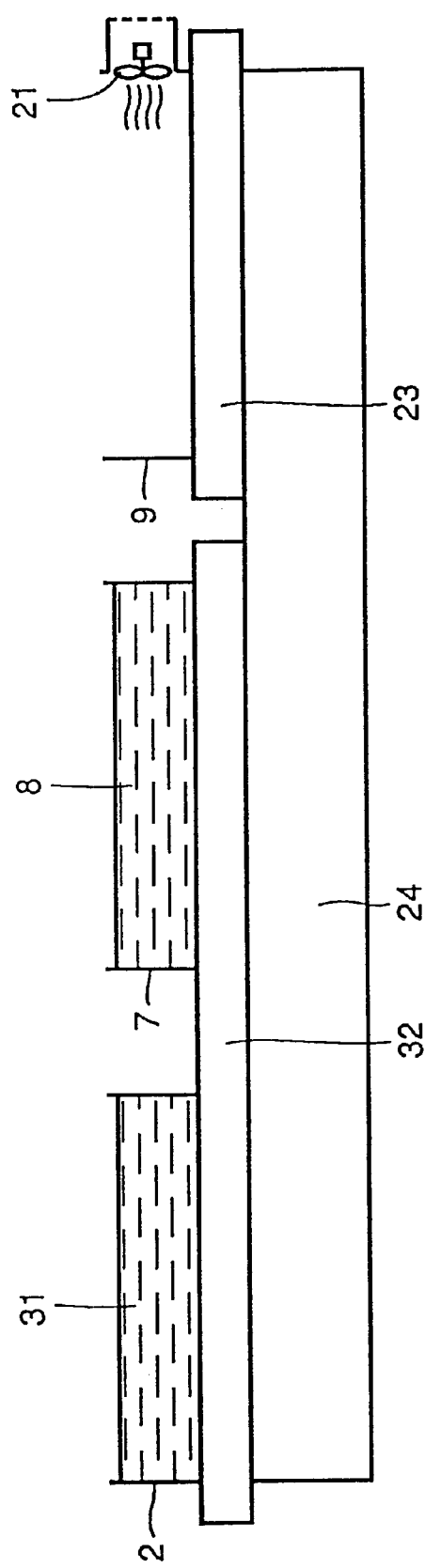
FIG. 15 schematically shows a cleaning device for a probe needle of a probe card according to a fourth embodiment of the present invention.
Figure 16:
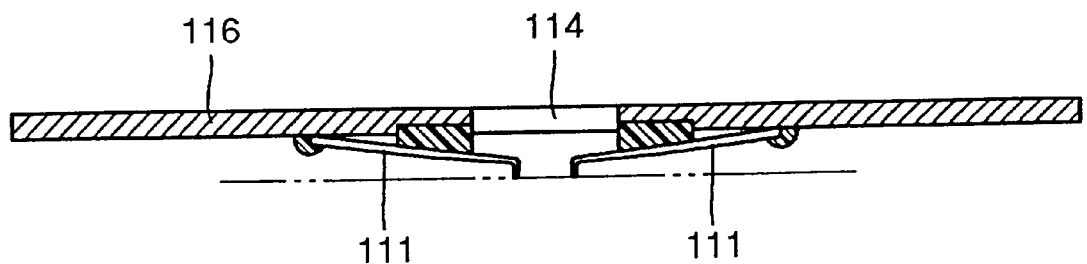
FIG. 16 is a cross sectional view illustrating a conventional probe card.
Figure 17:
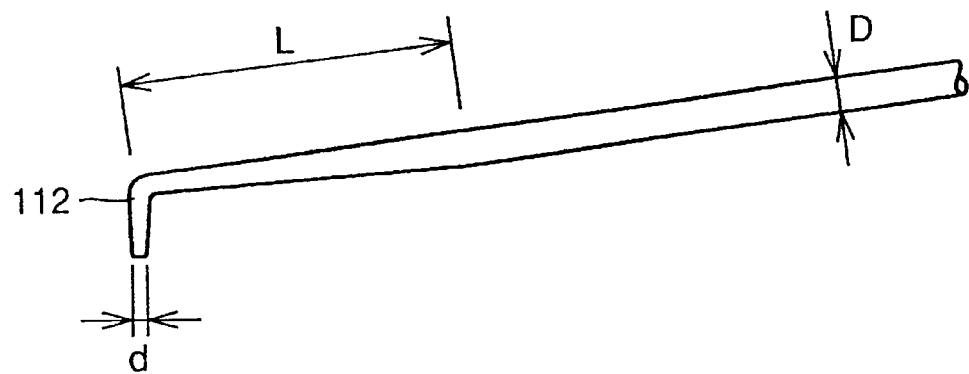
FIG. 17 is a schematic view illustrating a conventional probe needle.
Figure 18:
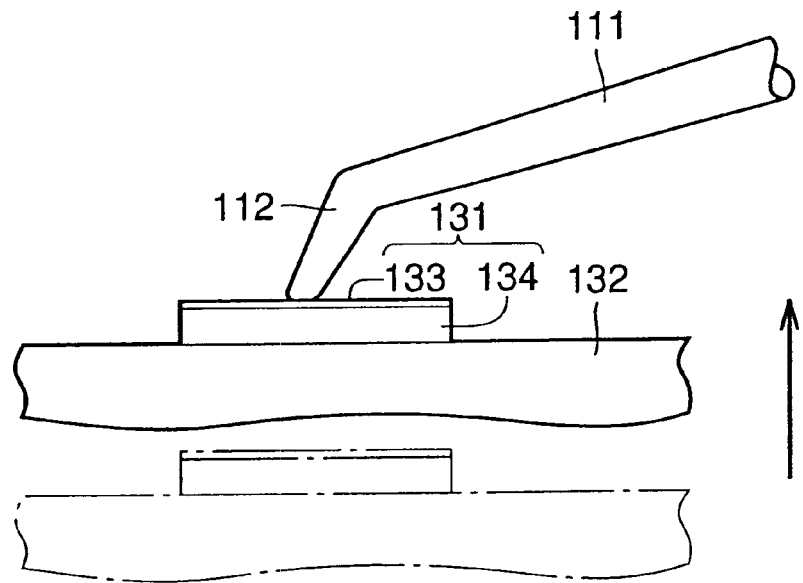
FIGS. 18 and 19 schematically show first and second steps of a process of bringing an electrode of a semiconductor device in contact with a probe needle in inspecting the electrical characteristics of the semiconductor device.
Figure 19:
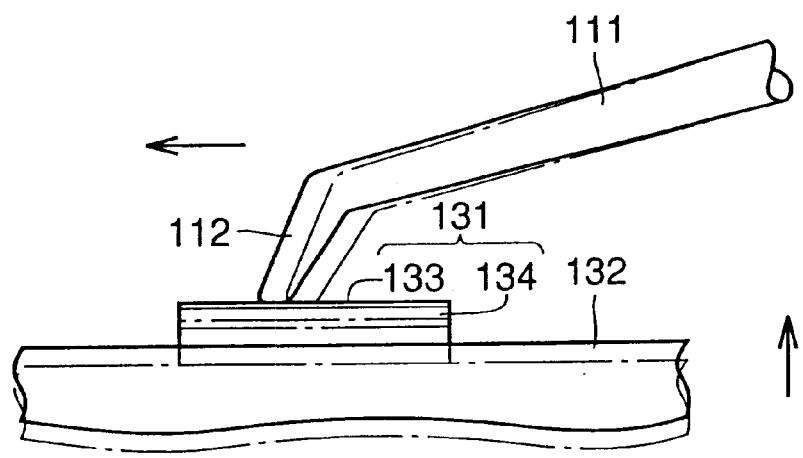
Figure 20:
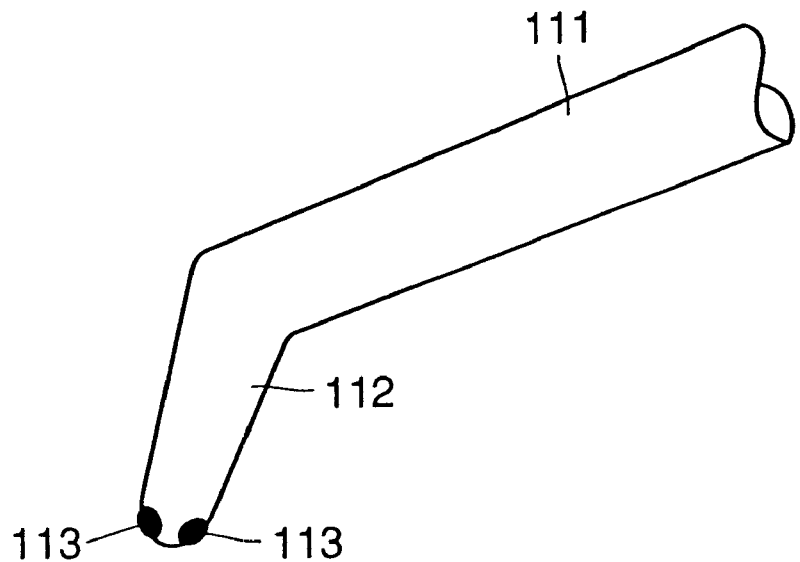
FIG. 20 schematically shows a foreign matter adhering to the tip of a probe needle.
Figure 21:
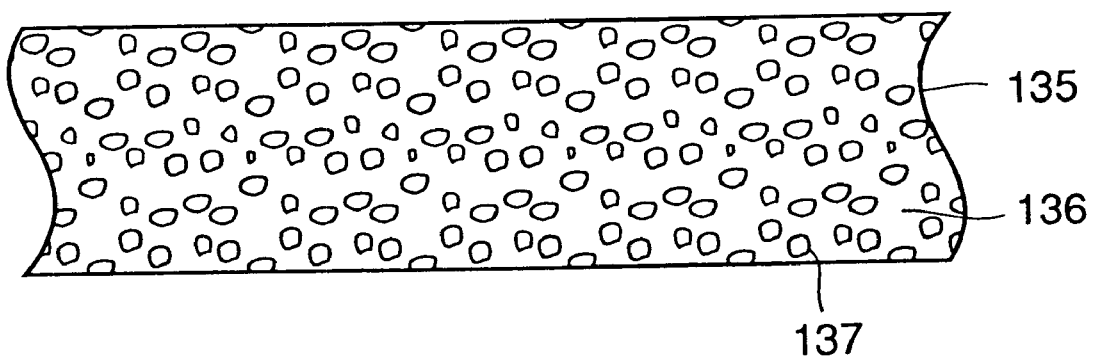
FIG. 21 schematically shows the cross section of a conventional abrasive sheet for a probe needle of a probe card.
Figure 22:
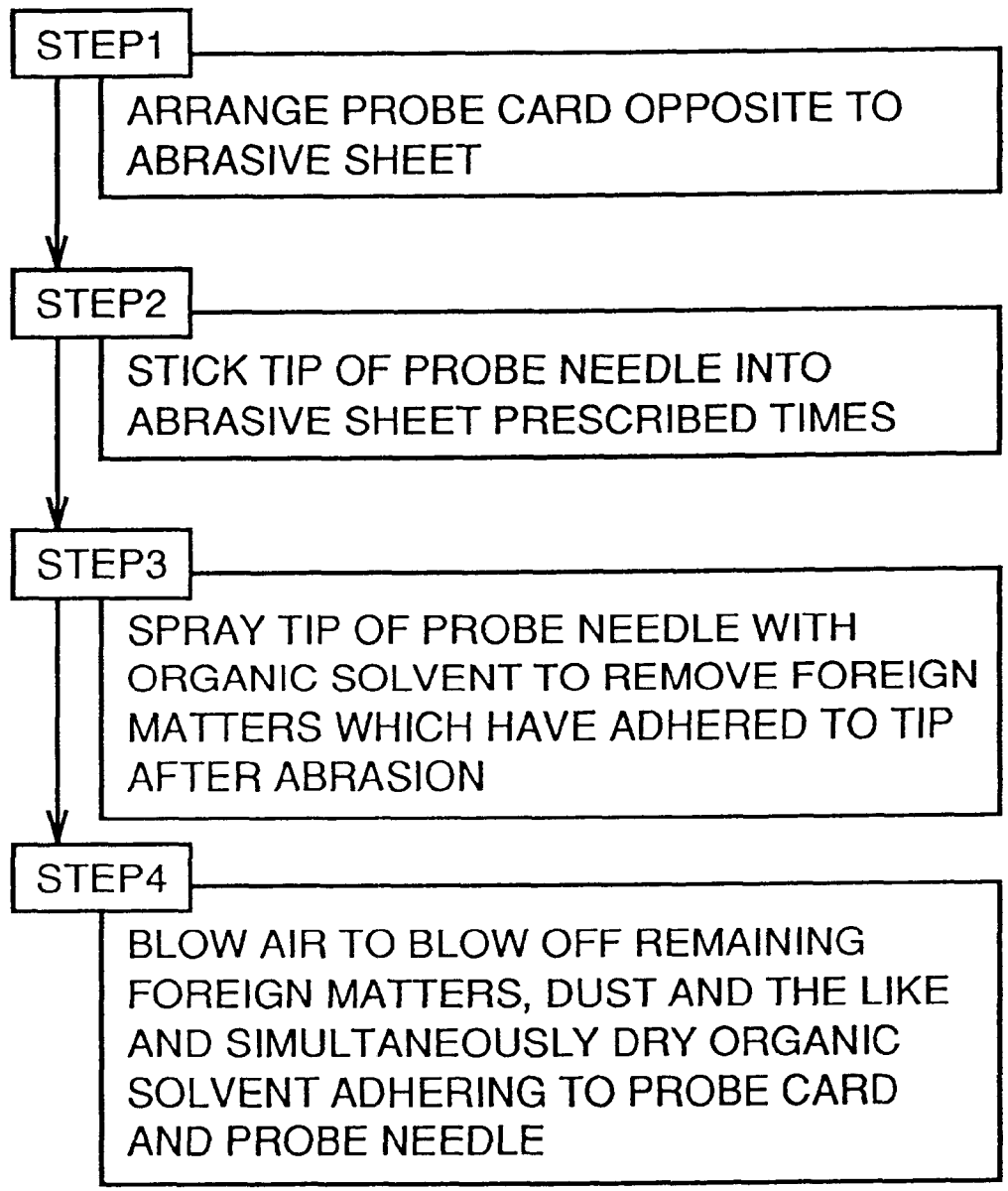
FIG. 22 is a flow chart of a cleaning operation for a probe needle of a probe card using the conventional abrasive sheet shown in FIG. 21.
Figure 23:
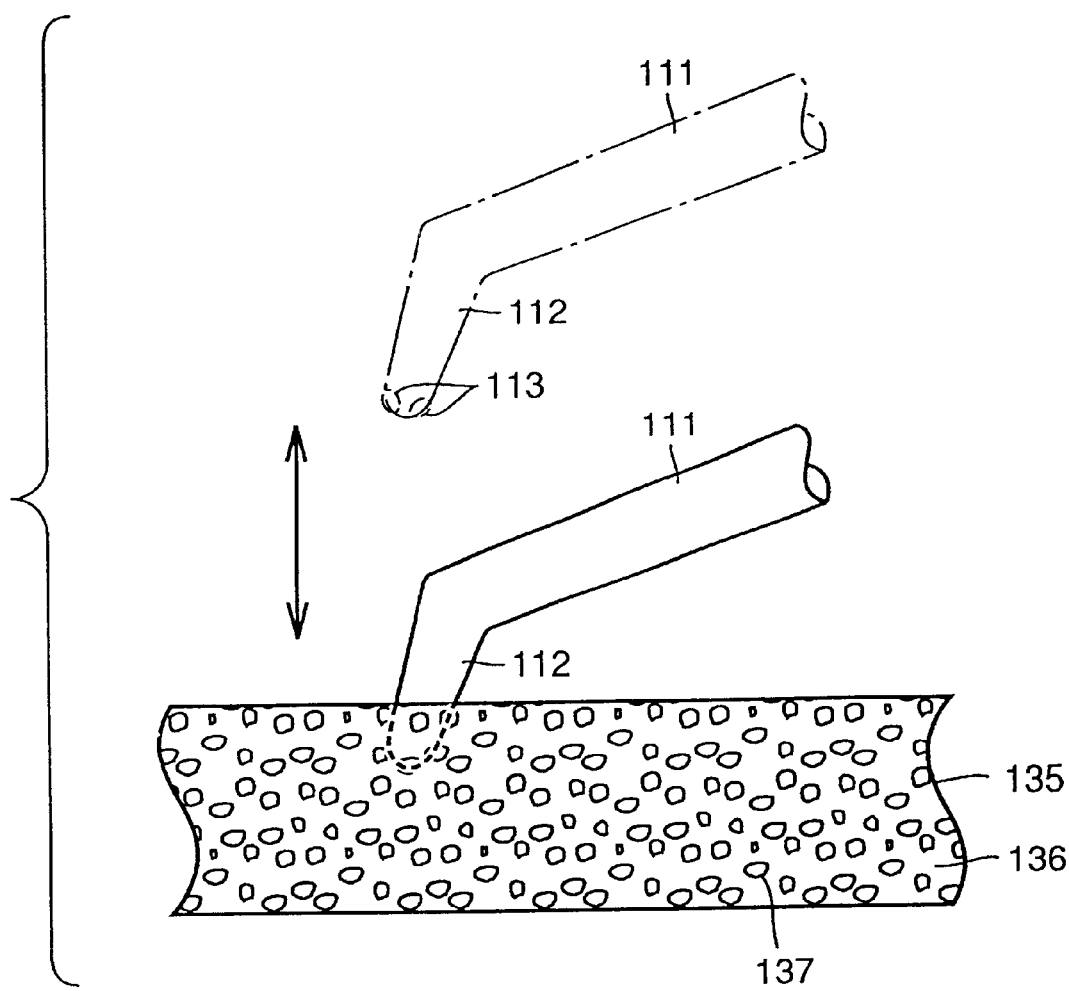
FIG. 23 schematically shows step 2 in the FIG. 22 conventional cleaning operation for a probe needle of a probe card.
Figure 24:
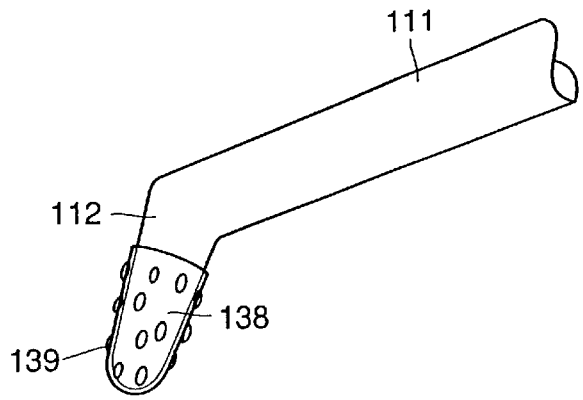
FIG. 24 schematically shows the state of a probe needle when step 2 is completed in the FIG. 22 conventional cleaning operation for a probe needle of a probe card.
Figure 25:
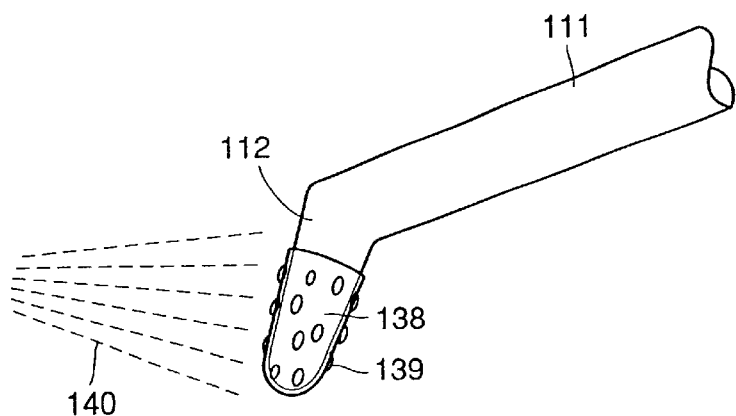
FIG. 25 schematically shows step 3 in the FIG. 22 conventional cleaning operation for a probe needle of a probe card.
Figure 26:
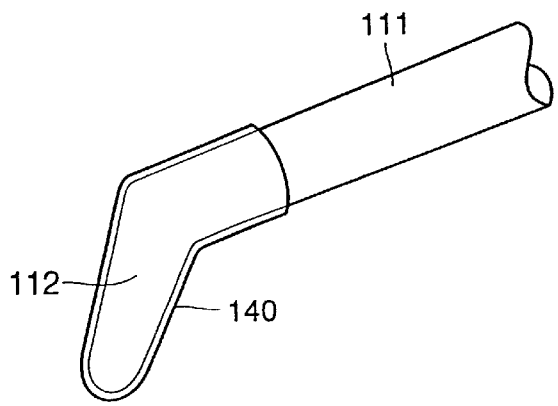
FIG. 26 schematically shows the state of a probe needle when step 3 is completed in the FIG. 22 conventional cleaning operation for a probe needle of a probe card.

Referring to FIG. 15, a cleaning device for a probe needle of a probe card according to a fourth embodiment of the present invention basically includes the same structure as the cleaning device for a probe needle of a probe card according to the second embodiment in the present invention. In the cleaning device according to the fourth embodiment shown in FIG. 15, however, a washing bath 2 is filled with a washing liquid 31 having the same composition as the washing liquid used in the third embodiment of the present invention. Since washing liquid 31 including an aqueous solution containing phosphoric acid allows a foreign matter to be removed from the tip of a probe needle while applying vibration by an ultrasonic generating device at a normal temperature, washing bath 2 does not require a member such as an electric heater. Accordingly, the structure of the cleaning device can be simplified.

By this structure, a probe needle with a foreign matter adhered can successively be immersed in washing liquid 31 in washing bath 2 and a processing liquid 8 such as alcohol in a post-processing bath 7 similarly to the cleaning device for a probe needle of a probe card according to the second embodiment shown in FIG. 7. Accordingly, a foreign matter can be removed from a probe needle with little abrasion and deformation of the tip of the probe needle. As a result, deformation and abrasion of the tip of a probe needle can be prevented and a probe needle life can be improved. When air is then blown to the probe needle by blower 21, the surface of the probe needle can be dried.

The same effect can be achieved even by applying a variation of the second embodiment of the present invention shown in FIGS. 8–13 to the cleaning device for a probe needle of the probe card according to the fourth embodiment of the present invention.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. A cleaning device for a probe needle of a probe card comprising:

a washing bath for storing a washing liquid for a probe needle including an aqueous solution containing chromic acid anhydride and phosphoric acid, wherein
      a ratio of said chromic acid anhydride with respect to water is 20 grams/1 liter, and
      a ratio of said phosphoric acid with respect to water is 36 milliliters/1 liter;
   said washing bath includes means for holding a surface of said washing liquid in which said probe needle is immersed higher than a surface other than the portion in which said probe needle is immersed.

2. A cleaning device for a probe needle of a probe card comprising:

a washing bath for storing a washing liquid for a probe needle including an aqueous solution containing chromic acid anhydride and phosphoric acid;
   said washing bath includes means for holding a surface of said washing liquid in which said probe needle is immersed higher than a surface other than the portion in which said probe needle is immersed,
   distance measuring means for measuring a distance between said probe needle and a surface of said washing liquid in said washing bath,
   position adjusting means for controlling a position of at least either of said probe needle and the surface of said washing liquid, and
   controlling means for controlling said position adjusting means based on information on the measured distance.

* * * * *